(12) United States Patent
Francke

(10) Patent No.: US 6,522,722 B1
(45) Date of Patent: Feb. 18, 2003

(54) COLLIMATION OF RADIATION FROM LINE-LIKE IONIZING RADIATION SOURCES AND PLANAR RADIATION BEAM DETECTION RELATED THERETO

(75) Inventor: Tom Francke, Sollentuna (SE)

(73) Assignee: XCounter AB, Danderyd (SE)

( * ) Notice: Subject to any disclaimer, the term of this patent is extended or adjusted under 35 U.S.C. 154(b) by 0 days.

(21) Appl. No.: 09/716,228

(22) Filed: Nov. 21, 2000

(30) Foreign Application Priority Data

Sep. 28, 2000 (SE) .............................................. 0003478

(51) Int. Cl.⁷ .............................................. G01T 1/185
(52) U.S. Cl. ........................ 378/146; 378/147; 250/374; 250/385.1
(58) Field of Search ........................... 378/57, 146, 62, 378/147; 250/385.1, 374

(56) References Cited

U.S. PATENT DOCUMENTS

| | | | |
|---|---|---|---|
| 4,096,389 A | | 6/1978 | Ashe et al. |
| 4,277,684 A | | 7/1981 | Carson |
| 4,864,594 A | | 9/1989 | Inbar et al. |
| 5,305,367 A | * | 4/1994 | Mulder ...................... 378/146 |
| 5,519,225 A | * | 5/1996 | Mohr et al. .................... 378/63 |
| 5,521,956 A | * | 5/1996 | Charpak ..................... 378/146 |
| 5,604,783 A | * | 2/1997 | Charpak ..................... 378/146 |
| 6,118,125 A | * | 9/2000 | Carlson et al. .......... 250/385.1 |
| 6,337,482 B1 | * | 1/2002 | Francke ................... 250/385.1 |
| 6,373,065 B1 | * | 4/2002 | Francke et al. .......... 250/385.1 |
| 6,385,282 B1 | * | 5/2002 | Francke et al. ................ 378/51 |
| 6,389,103 B2 | * | 5/2002 | Francke et al. ................ 378/98 |
| 6,414,317 B1 | * | 7/2002 | Francke et al. .......... 250/385.1 |

FOREIGN PATENT DOCUMENTS

| | | |
|---|---|---|
| DE | 40 26 299 A1 | 2/1992 |
| GB | 2 004 448 A | 3/1979 |
| WO | 99/23859 | 5/1999 |

* cited by examiner

Primary Examiner—Drew A. Dunn
(74) Attorney, Agent, or Firm—Birch, Stewart, Kolasch & Birch, LLP

(57) ABSTRACT

An apparatus for planar beam radiography comprises an ionizing radiation source and an ionizing radiation detector; the ionizing radiation source being line-like and extending substantially in a first direction; and the ionizing radiation comprising an elongated radiation slit entrance extending substantially in a second direction and being arranged for one-dimensional detection of radiation from the radiation source entering the detector through the radiation slit entrance. According to the present invention the radiation source and the radiation dectector are oriented such that the first and second directions are essentially perpendicular. Hereby,a facilitated alignment of the detector with respect to source is achieved.

21 Claims, 2 Drawing Sheets

COLLIMATION OF RADIATION FROM LINE-LIKE IONIZING RADIATION SOURCES AND PLANAR RADIATION BEAM DETECTION RELATED THERETO

TECHNICAL FIELD OF THE INVENTION

The present invention generally relates to collimation of radiation from line-like radiation sources such as e.g. X-ray sources, and to alignment of radiation detectors thereto.

More specifically, the invention relates to arrangements and methods for producing a planar radiation beam of ionizing radiation emanating from a line-like X-ray source, to apparatus for planar beam radiography using such planar radiation beam, and to methods of aligning a detector with respect to a radiation source.

DESCRIPTION OF RELATED ART AND BACKGROUND OF THE INVENTION

Gaseous-based ionizing radiation detectors, in general, are very attractive at low photon energies since they are cheap to manufacture, and since they can employ gas multiplication to strongly amplify the signal amplitudes. A particular kind of gaseous detector is the one, in which electrons released by interactions between photons and gas atoms can be extracted in a direction essentially perpendicular to the incident radiation. Such detector is typically a line detector provided with an elongated narrow radiation entrance slit which collimates incident radiation from a point-like radiation source into a planar beam of radiation. A two-dimensional image is then typically obtained through scanning. Optionally, a further collimator, parallel with the detector radiation entrance slit, is arranged between the radiation source and the detector.

One problem encountered when using such detectors is the difficulties obtained in aligning the detector, and possibly the collimator, with respect to the radiation source. Such alignment has to be very accurate and precise and any misalignment results inevitably in the need of realignment. Typically the detector and/or the collimator has to be aligned prior to each single measurement, which is both costly and time-consuming. Further, particular alignment means, such as e.g. optical alignment devices, may have to be provided.

SUMMARY OF THE INVENTION

Accordingly, it is an object of the present invention to provide an apparatus for planar beam radiography which can be easier and faster aligned than prior art apparatus.

It is in this respect a particular object of the invention to provide such apparatus for planar beam radiography that provides for faster and thus cheaper measurements.

A further object of the present invention is to provide such apparatus for planar beam radiography, which is effective, accurate, reliable, and which can be implemented in a simple and cost effective way.

Yet a further object of the present invention is to provide an arrangement for producing a planar beam of ionizing radiation, which can be fast and easy aligned.

Still a further object of the invention is to provide a method for aligning an ionizing radiation detector with respect to a radiation source, which is easier and faster than prior art alignment techniques.

Yet a further object of the present invention is to provide a method for producing a planar beam of ionizing radiation, which is fast and easily performed.

These objects among others are attained by apparatus, methods, and arrangements as claimed in the appended claims.

Further characteristics of the invention and advantages thereof will be evident from the following detailed description of preferred embodiments of the invention, which are shown in the accompanying drawings.

BRIEF DESCRIPTION OF THE DRAWINGS

The present invention will become more fully understood from the detailed description of embodiments of the present invention given hereinbelow and the accompanying FIGS. 1–4 which are given by way of illustration only, and thus are not limitative of the invention.

DETAILED DESCRIPTION OF PREFERRED EMBODIMENTS

Figure 1:
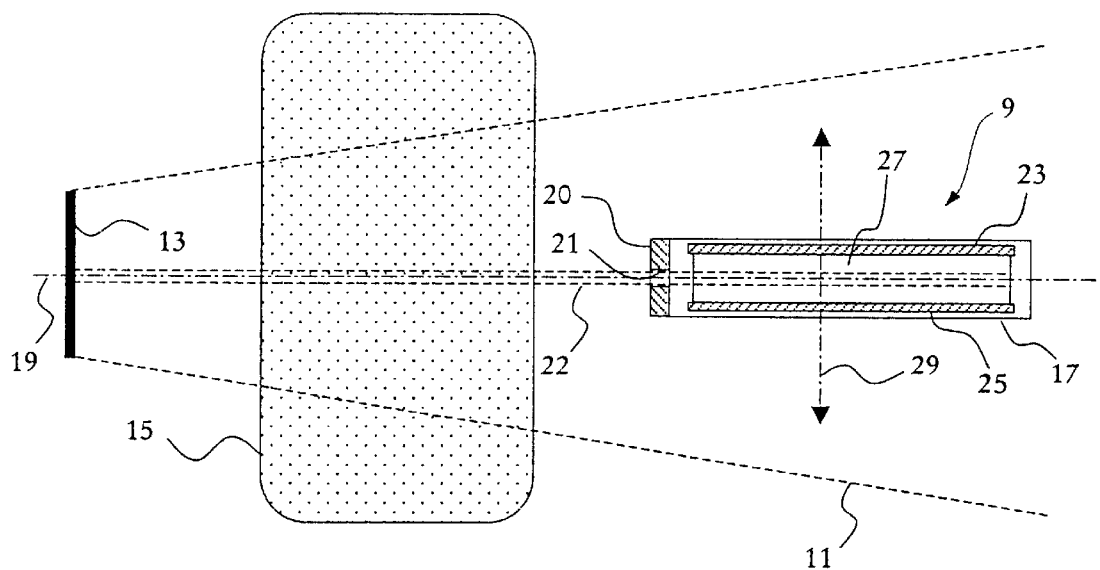
FIG. 1 illustrates schematically, in a cross-sectional side view with detector parts cut-away, an apparatus for planar beam radiography according to a first embodiment of the present invention.
Figure 2:
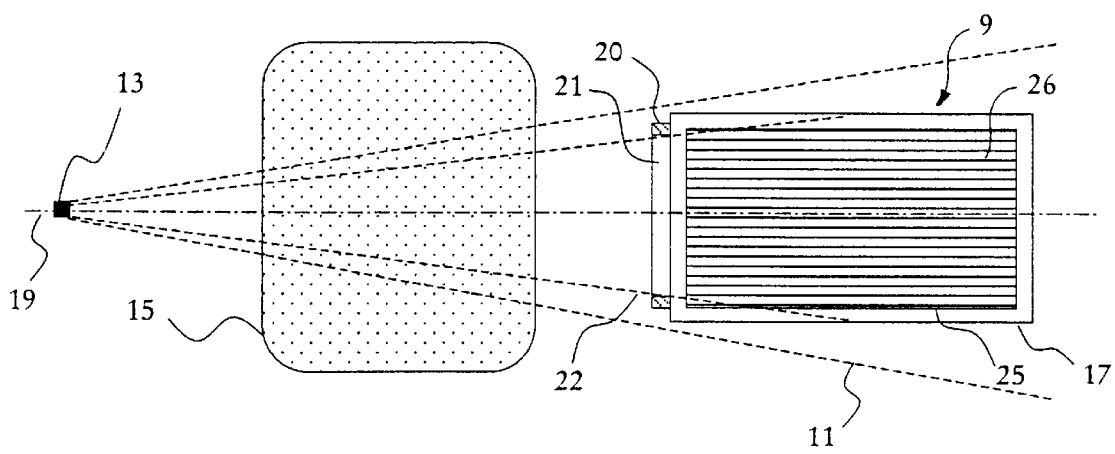
FIG. 2 illustrates schematically, in a cross-sectional top view with detector parts cut-away, the apparatus of FIG. 1.

With reference to FIGS. 1 and 2, which schematically illustrate, in cross-sectional side and top views, respectively, with detector parts cut-away, an apparatus for planar beam radiography, a first embodiment of the present invention will be described.

The apparatus for planar beam radiography comprises a radiation detector 9 including a substantially planar cathode 23 and anode 25, respectively, between which a voltage is capable of being applied, and an ionizable substance 27 arranged between cathode 23 and anode 25. The electrodes 23 and 25 and the ionizable substance 27 are typically confined in a casing 17. Further, a collimator 20 having an elongated radiation transparent slit 21 extending essentially parallel with the electrodes 23 and 25 such that radiation can enter sideways between and in parallel with the electrodes.

The ionizable substance 27 can be a gas or gas mixture comprising for example 90% krypton and 10% carbon dioxide or for example 80% xenon and 20% carbon dioxide. The gas can be under pressure, preferably in a range 1–20 atm. Thus, casing 17 is preferably a gas tight casing provided with a radiation entrance window of a radiation transparent material. Alternatively, ionizable substance 27 is a semiconducting material such as e.g. silicon or a higher Z semiconducting material.

Anode 25 includes a plurality of elongated conductive pads 26 arranged side by side, which is best seen in FIG. 2. Pads 26 are preferably arranged electrically insulated from each other on a dielectric substrate. Anode 25 constitutes also a read-out arrangement of the detector and thus conductive pads 26 constitute read-out elements for one-dimensional mapping of electrons drifted or accelerated towards the anode 25. Alternatively, a separate read-out arrangement is provided or a separate read-out arrangement may be arranged in vicinity of anode 25, in vicinity of cathode 23, or elsewhere. Typically, such read-out arrangement is separated from the electrode by a dielectric layer, or similar.

It shall be appreciated that the read-out elements are arranged in a way to compensate for the divergence of any incoming radiation. Thus, the read-out elements may be arranged in a fan-like configuration, wherein each of the elements is aiming at the radiation source of the incoming radiation.

Further, the read-out arrangement is connected to a signal processing device (not illustrated) for necessary and/or desired post-processing of collected signal data. Preferably, the read-out elements 26 are then separately connected to the signal processing circuit by means of individual signal conduits. A signal display unit (neither illustrated) is provided for displaying the processed signal data.

In operation, a sheet of radiation is entered into the ionizable substance through slit 21 of collimator 20, the radiation ionizing the ionizable substance 27. A voltage is applied between cathode 23 and anode 25 resulting in electrical field, which causes electrons released from ionization (through primary and secondary reactions) to drift towards the anode 25. Correspondingly produced positive charge carriers (i.e., ions or holes) are drifted towards the cathode 23. The electrons induce electric pulses in the anode or read-out elements 26, which are individually detected as each read-out element has its individual signal conduit to the signal processor. The signal processing electronics processes the pulses; it possibly shapes the pulses, and integrates or counts the pulses from each readout element. Correspondingly, the positive charge carriers induce pulses that may alternatively, or additionally, be detected.

By providing a one-dimensional array of read-out elements 26 a radiation detector is obtained, wherein charge carriers derivable mainly from ionization by transversely separated portions of the incident radiation sheet are separately detectable. Hereby, the detector provides for one-dimensional imaging.

In order to more easily align the detector 9 the apparatus for planar beam radiation comprises a line-like ionizing radiation source 13, preferably an X-ray source, oriented such that it extends essentially perpendicular to the extension of radiation entrance slit 21 of detector 9. The divergent radiation beam 11 emanating from radiation source 13 makes it possible to produce a sheet-shaped radiation beam 22 by means of radiation entrance slit 21 in a plane orthogonal to the direction of extension of line-like radiation source 13. Thus, sheet-shaped radiation beam 22 is entered into the detector 9 to interact with the ionizable substance 27 therein.

Further, an object 15 to be imaged is arranged in the radiation path of radiation beam 11 between radiation source 13 and detector 9. Object 15 is preferably not a living organism, but other material under investigation, as the object is exposed to considerable radiation dose. Alternatively, the radiation source and the detector are arranged such that radiation beam 11 as reflected off object 15 is impinging onto the detector 9 and a portion thereof is entered through the entrances slit (not illustrated).

By such provisions (i.e. mutual orientation), the alignment of the detector 9 with respect to the radiation source is considerably facilitated. This is in FIG. 1 schematically indicated by means of possible movement of detector 9 as defined by arrow 29 substantially perpendicular to central axis 19, while the detector still "sees" the radiation source and is thus maintained in alignment with the radiation source. The object is here preferably assumed to be larger or much larger than the dimension of the radiation source. Otherwise the object puts restrictions on the alignment tolerances allowed.

If the arrangement of FIG. 1 is to be used for imaging of a living organism, or a portion thereof, e.g. a patient body part, the radiation source 13 has a maximum length allowed such that the radiation dose exposed to the organism does not exceed a predetermined level, e.g. a limit value allowed.

The line-like radiation source 13 has a length preferably of at least 0.1 mm, more preferably of at least 1 mm, even more preferably of at least 10 mm, and most preferably of about 50 mm. The width of the line-like radiation source 13 may vary from e.g. about 0.05 mm to 2 mm, and is typically about 0.1 mm. However, it shall be appreciated that the present invention is not restricted to these given focal spot sizes.

The elongated radiation slit entrance 21 has a height, i.e. a dimension in the direction of arrow 29, preferably of 0.01–5 mm, more preferably of 0.02–1 mm, even more preferably of 0.02–0.3 mm, and most preferably of about 0.05 mm, and a thickness, i.e. a dimension in the direction of the radiation 22 entering detector 9, preferably of 0.01–5 mm, more preferably of 0.05–1 mm, and most preferably of 0.05–0.3 mm. The length of radiation slit entrance 21, i.e. a dimension in a direction perpendicular to the direction of arrow 29 and to the direction of the radiation 22 entering detector 9, may range within a tremendously large interval depending on the application in which the arrangement is to be employed.

Further, a two-dimensional image is typically obtained through scanning. The scanning is preferably made in a pivoting movement around any axis, but preferably an axis passing through the X-ray source or its vicinity. The scanning can also be transversal in the direction of arrow 29. Measurements performed at different positions provide each information of a particular splice through object 15 and thus a two-dimensional image may be reconstructed without the need of moving the radiation source 13 or the object 15 to be imaged. As radiation source 13 possibly has an intensity and a wavelength spectrum that vary along its extension, different techniques to compensate for this may be applied.

It shall be appreciated that a plurality of the inventive detector 9 may be stacked, side-by-side of each other. By such provision multi-line scans can be performed, which reduces the overall scanning distance, as well as the scanning time. Further reference in this respect is made to our co-pending Swedish patent application 0000388-9 entitled Detector and method for detection of ionizing radiation and filed on Feb. 08, 2000, said application being hereby incorporated by reference.

Figure 3:
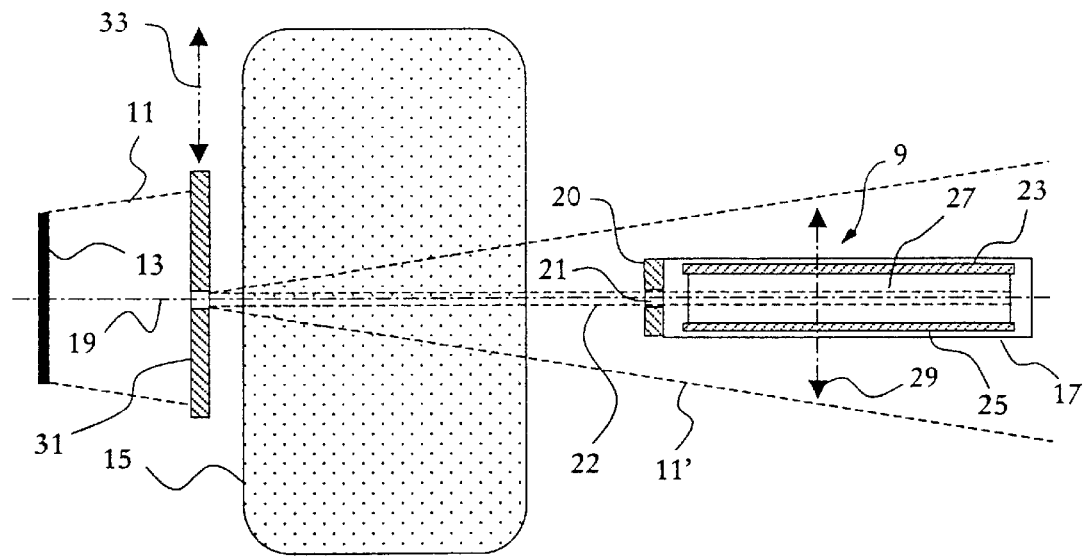
FIG. 3 illustrates schematically, in a cross-sectional side view with detector parts cut-away, an apparatus for planar beam radiography according to a second embodiment of the present invention.
Figure 4:
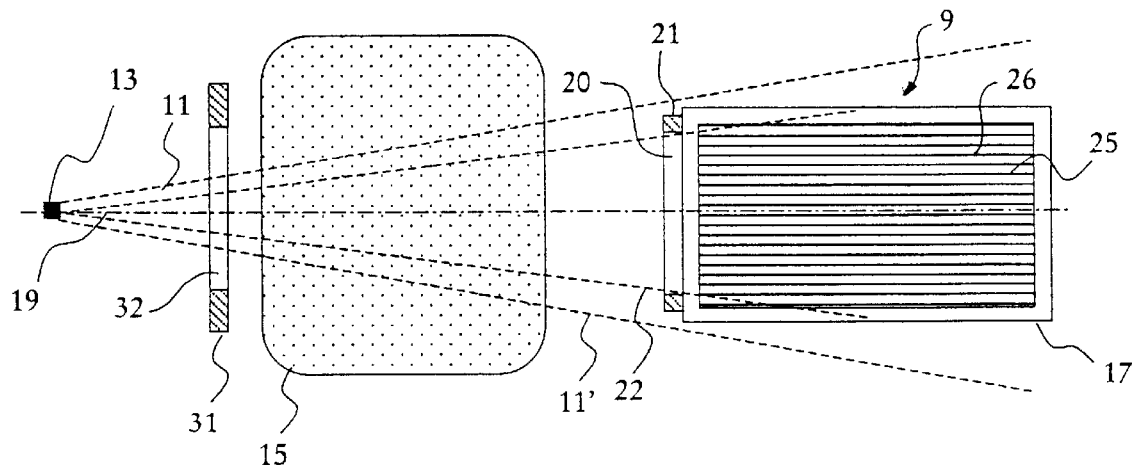
FIG. 4 illustrates schematically, in a cross-sectional top view with detector parts cut-away, the apparatus of FIG. 3.

With reference to FIGS. 3 and 4, which schematically illustrate, in cross-sectional side and top views, respectively, with detector parts cut-away, an apparatus for planar beam radiography, a second embodiment of the present invention will be described. This second embodiment differs from the previous embodiment as regards the following features.

The apparatus of FIGS. 3 and 4 further comprises a collimator 31 having an elongated radiation transparent slit 32 extending essentially parallel with the entrance slit 21 of detector 9. Collimator 31 is arranged between radiation source 13 and object 15 to be imaged such that radiation beam 11 from radiation source 13 is firstly collimated by the collimator 31. The radiation beam passing through collimator 31, denoted 11' in FIGS. 3 and 4, is transmitted through object 15 to be imaged. Radiation slit entrance 21 of detector 9 is operating as a second collimator to further collimate radiation beam and the planar radiation beam entered into detector 9 is as in previous embodiment denoted by 22.

The dimensions of collimator slit 32 are preferably similar to those of detector radiation entrance slit 21.

The alignment of detector 9 and collimator 31 with respect to each other and with respect to radiation source is slightly more complicated than the alignment necessitated in the FIGS. 1 and 2 embodiment. Either one of detector 9 or collimator 31 is firstly aligned with respect to the radiation source (alignment movements of detector 9 and collimator 31, respectively, are indicated by arrows 29 and 33). This alignment is easy as it is sufficient to align the detector or the collimator so as to obtain a planar radiation beam into the detector or through the collimator. The ease of such alignment is directly dependent on the extension of radiation source (if not a very small object to be imaged puts restrictions in this respect). Subsequently thereto, the other one of the detector or the collimator is aligned, and this alignment has to be performed more accurately.

In this second embodiment a large amount of the radiation 11 emanating from radiation source 13 is shielded from reaching object 15, and thus this embodiment is suitable for diagnostical purposes as the patient dose will be lower.

Nevertheless, the object 15 is exposed to a higher dose than if a point-like radiation source is used. Thus, it is adequate to state that the alignment is easier the longer the radiation source, whereas the radiation exposed to object 15 is higher the longer the radiation source is. Thus an optimal length of radiation source 13 exists for each application.

How to select an appropriate radiation source is thus a crucial task; one way is to use a maximum radiation source length that fulfils a given maximum exposed radiation dose allowed.

In a general case a first cost function related to the ease of alignment may be determined, wherein a long radiation line-like radiation source provides for a lower cost than a short linelike radiation source. A second cost function related to the radiation dose exposed to object 15 is correspondingly determined, wherein a long line-like radiation source provides for a higher cost than a short line-like radiation source. To find an optimal radiation source given the cost functions, the sum of these cost functions is calculated, whereafter the length of line-like radiation source 13 is selected so as to minimize the sum of the cost functions.

It shall be appreciated that the beam shapes as indicated in the Figs. are strongly simplified for illustrative purposes. The divergence of a radiation beam is in a general case complicated to calculated as is well recognized by the man skilled in the art.

It will be obvious that the invention may be varied in a plurality of ways. Such variations are not to be regarded as a departure from the scope of the invention. All such modifications as would be obvious to one skilled in the art are intended to be included within the scope of the appended claims.

What is claimed is:

1. An apparatus for planar beam radiography comprising an ionizing radiation source and an ionizing radiation detector;
   said ionizing radiation source being line-like and extending substantially in a first direction; and
   said ionizing radiation detector comprising an elongated radiation slit entrance extending substantially in a second direction and being arranged for one-dimensional detection of radiation from said radiation source entering said detector through said radiation slit entrance, wherein
   said first and second directions are essentially perpendicular.

2. The apparatus as claimed in claim 1, wherein said ionizing radiation source and said ionizing radiation detector are arranged such that radiation from said ionizing radiation source as transmitted through, or reflected off, an object to be imaged is entered into said detector through said radiation slit entrance.

3. The apparatus as claimed in claim 2, wherein said ionizing radiation source has an extension in substantially said first direction such that the radiation dose exposed to said object does not exceed a predetermined level.

4. The apparatus as claimed in claim 2, further comprising a collimator having an elongated radiation transparent slit extending essentially parallel with said second direction, said collimator being arranged between said radiation source and the object to be imaged such that said radiation from said radiation source transmitted through, or reflected off, the object to be imaged and entered into the detector through the radiation slit entrance is initially passed through said radiation transparent slit of said collimator.

5. The apparatus as claimed in claim 4, wherein said elongated radiation transparent slit extending essentially parallel with said elongated radiation slit entrance has a dimension in said first direction of 0.01–5 mm.

6. The apparatus as claimed in claim 1, wherein said ionizing radiation source has an extension in substantially said first direction of at last 0.1 mm.

7. The apparatus as claimed in claim 1, wherein said elongated radiation slit entrance extending substantially in a second direction has a dimension in said first direction of 0.01–5 mm.

8. The apparatus as claimed in claim 1, wherein said elongated radiation slit entrance extending substantially in a second direction has a dimension in a third direction of 0.01–5 mm, said third direction being perpendicular to said first and said second directions.

9. The apparatus as claimed in claim 1, wherein said ionizing radiation detector comprises an excitable or ionizable substance arranged such that said radiation entering said detector through said radiation slit entrance is entered into said substance; and a read-out arrangement for detection of charge carriers created during ionization of said ionizable substance, or of photons released subsequent to excitation of said excitable substance, in a direction essentially perpendicular to said entered radiation.

10. A method of aligning an ionizing radiation detector with respect to a radiation source, said method comprising the steps of:
   providing an ionizing radiation detector comprising an elongated radiation slit entrance extending substantially in a first direction and being arranged for one-dimensional detection of radiation entering said detector through said radiation slit entrance; and
   providing an ionizing radiation source being line-like and extending substantially in a second direction,
   arranging said ionizing radiation detector and said ionizing radiation source with respect to each other such that said first and second directions are essentially perpendicular; and
   aligning said ionizing radiation detector with respect to said ionizing radiation source such that radiation from said radiation source enters said detector through said radiation slit entrance.

11. The method as claimed in claim 10, wherein radiation from said ionizing radiation source entered into said detector through said radiation slit entrance is passed through, or scattered off, an object to be imaged prior to being entered into said detector.

12. The method as claimed in claim 10, wherein said ionizing radiation from said ionizing radiation source entered into said detector through said radiation slit entrance is passed through an elongated radiation transparent collimator slit extending essentially parallel with said second radiation slit entrance prior to being passed through, or scattered off, an object to be imaged.

13. The method as claimed in claim 11, wherein the extension of said ionizing radiation source in substantially said first direction is selected such that the radiation dose exposed to said object does not exceed a predetermined level.

14. A method of producing a planar beam of ionizing radiation emanating from a line-like ionizing radiation source extending substantially in a first direction, said method comprising the steps of:

arranging a first elongated radiation transparent collimator slit extending substantially in a second direction such that said first and second directions are perpendicular; and aligning said first elongated radiation transparent collimator slit with respect to said ionizing radiation source such that radiation from said ionizing radiation source passes through said first collimator slit.

15. The method as claimed in claim 14, further comprising:

arranging a second elongated radiation transparent collimater slit extending substantially in a third direction such that said second and third direction are parallel; and aligning said second elongated radiation collimater slit with respect to said first collimator slit such that at least a portion of the radiation passed through said first transparent collimator slit passes through said second collimator slit.

aligning said first elongated radiation transparent collimator slit with respect to said ionizing radiation source such that radiation from said ionizing radiation source passes through said first collimator slit.

16. The method as claimed in claim 14, wherein radiation passed through said first transparent collimator slit is passed through, or scattered off, an object.

17. The method as claimed in claim 15, wherein said second collimator slit is a radiation slit entrance of a radiation detector.

18. An arrangement for producing a planar beam of ionizing radiation comprising an ionizing radiation source and a first elongated radiation transparent collimator slit, said ionizing radiation source being line-like and extending substantially in a first direction; and said first collimator slit extending substantially in a second direction, wherein said first collimator is arranged with respect to said ionizing radiation source such that said first and second directions are essentially perpendicular; and said first collimator is aligned with respect to said ionizing radiation source such that radiation from said source passes through said first collimator slit.

19. The arrangement as claimed in claim 18, further comprising a second elongated radiation transparent collimator slit extending substantially in a third direction, said second collimator slit being arranged with respect to said first collimator slit such that said second and third directions are parallel; and said second elongated collimator slit being aligned with respect to said first collimator slit such that radiation passed through said first transparent collimator slit passes through said second collimator slit.

20. The arrangement as claimed in claim 19, wherein said first collimator slit is arranged such that radiation passed through said first collimator slit can pass through, or be scattered off, an object.

21. The arrangement as claimed in claim 20, wherein said second collimator slit is a radiation slit entrance of a radiation detector.

* * * * *